(12) United States Patent
Morimoto

(10) Patent No.: US 8,300,018 B2
(45) Date of Patent: Oct. 30, 2012

(54) TACTILE SENSOR

(75) Inventor: Kenichi Morimoto, Kyoto (JP)

(73) Assignee: Ewsystem Co., Ltd., Kyoto (JP)

( * ) Notice: Subject to any disclaimer, the term of this patent is extended or adjusted under 35 U.S.C. 154(b) by 881 days.

(21) Appl. No.: 11/990,759

(22) PCT Filed: Sep. 5, 2005

(86) PCT No.: PCT/JP2005/016272
§ 371 (c)(1),
(2), (4) Date: Feb. 21, 2008

(87) PCT Pub. No.: WO2007/029305
PCT Pub. Date: Mar. 15, 2007

(65) Prior Publication Data
US 2008/0271933 A1 Nov. 6, 2008

(51) Int. Cl.
*G06F 3/041* (2006.01)
(52) U.S. Cl. .................. 345/173; 345/156
(58) Field of Classification Search .......... 345/173, 345/156; 338/205, 247; 178/18.05
See application file for complete search history.

(56) References Cited

U.S. PATENT DOCUMENTS

| | | | |
|---|---|---|---|
| 4,014,217 A | 3/1977 | Lagasse et al. | |
| 4,687,885 A * | 8/1987 | Talmage et al. | 178/18.05 |
| 5,159,159 A | 10/1992 | Asher | |
| 5,694,154 A * | 12/1997 | Knox et al. | 345/173 |
| 6,239,790 B1 * | 5/2001 | Martinelli et al. | 345/174 |
| 6,781,576 B2 * | 8/2004 | Tamura | 345/173 |
| 6,861,961 B2 * | 3/2005 | Sandbach et al. | 341/22 |
| 7,209,028 B2 * | 4/2007 | Boronkay et al. | 338/205 |
| 7,248,249 B2 * | 7/2007 | Kong et al. | 345/173 |
| 2004/0055396 A1 * | 3/2004 | Morimoto | 73/862.045 |

FOREIGN PATENT DOCUMENTS

| | | |
|---|---|---|
| JP | 59-110595 A | 6/1984 |
| JP | 59-178301 A | 10/1984 |
| JP | 60-71194 A | 4/1985 |
| JP | 60-35602 B2 | 8/1985 |
| JP | 60-35604 B2 | 8/1985 |
| JP | 60-37401 B2 | 8/1985 |
| JP | 61-47501 A | 3/1986 |
| JP | 61-32601 B2 | 7/1986 |
| JP | 61-208533 A | 9/1986 |
| JP | 3-55448 A | 3/1991 |

(Continued)

*Primary Examiner* — Quan-Zhen Wang
*Assistant Examiner* — Calvin C Ma
(74) *Attorney, Agent, or Firm* — Birch, Stewart, Kolasch & Birch, LLP

(57) ABSTRACT

A tactile sensor for detecting a variation in pressing real-time. The tactile sensor is simple in structure, detects a variation in pressing by using reduced wires, has increased reliability and reduced cost, and can obtain information accurately. A sheet has, along its surface, resistors arranged in an X direction and Y direction, has a resistor in Z direction corresponding to the thickness direction of the sheet, and has a pressure sensitive resistor sheet (4) whose resistance in the Z direction varies according to pressing in the thickness direction. At least a pair of electrodes (9, 10, 11, 12) is placed in the periphery of the pressure sensitive sheet (4), and the electrodes conduct a current to at least either of the resistor in the X direction or the resistor in the Y direction. Also, at least a pair of conductors (5, 6) for conducting a current to the resistor in the Z direction is provided on the surface of the pressure sensitive sheet (4).

5 Claims, 11 Drawing Sheets

FOREIGN PATENT DOCUMENTS

| | | |
|---|---|---|
| JP | 5-61592 A | 3/1993 |
| JP | 6-35604 A | 2/1994 |
| JP | 6-147501 A | 5/1994 |
| JP | 7-58233 B2 | 6/1995 |
| JP | 10-178688 A | 6/1998 |
| JP | 11-212712 A | 8/1999 |
| JP | 3055448 B2 | 6/2000 |

* cited by examiner

FIG.4 CONCEPTUAL DIAGRAM SHOWING ONE EXAMPLE OF CONTACT AREA DETECTION

WHEN CONTACT POSITION IS NEAR THE CENTER

WHEN CONTACT POSITION IS NEAR THE PERIPHERY

FIG.13

| SWITCH SW ORDER | 11 | 12 | 13 | 14 | USE IN USE/NOT USE | FUNCTION |
|---|---|---|---|---|---|---|
| 5 | 0 | 0 | 0 | 0 | IN USE | X COORDINATE DETECTION |
| 4 | 0 | 0 | 0 | 1 | IN USE | Y COORDINATE DETECTION |
|   | 0 | 0 | 1 | 0 | NOT USE |   |
|   | 0 | 0 | 1 | 1 | NOT USE |   |
|   | 0 | 1 | 0 | 0 | NOT USE | POWER SUPPLY SHORT CIRCUIT |
|   | 0 | 1 | 0 | 1 | NOT USE | POWER SUPPLY SHORT CIRCUIT |
|   | 0 | 1 | 1 | 0 | NOT USE | POWER SUPPLY SHORT CIRCUIT |
|   | 0 | 1 | 1 | 1 | NOT USE | POWER SUPPLY SHORT CIRCUIT |
| 3 | 1 | 0 | 0 | 0 | NOT USE | SINCE SIMULTANEOUS SWITCHOVER OF SW11 AND SW12 MAKES A SHORT CIRCUIT, FIRST SWITCH SW2 AND THEN SWITCH SW3 |
|   | 1 | 0 | 0 | 1 | NOT USE |   |
|   | 1 | 0 | 1 | 0 | NOT USE |   |
|   | 1 | 0 | 1 | 1 | NOT USE |   |
|   | 1 | 1 | 0 | 0 | NOT USE |   |
| 2 | 1 | 1 | 0 | 1 | IN USE | CONTACT AREA DETECTION |
|   | 1 | 1 | 1 | 0 | NOT USE |   |
| 1 | 1 | 1 | 1 | 1 | IN USE | Z COORDINATE(PRESSING)DETECTION |

TACTILE SENSOR

TECHNICAL FIELD

The present invention relates to detection and control of input information of pressure and its position, and relates to a tactile sensor for detecting contact coordinates, contact pressure, and contact length by a simple method and a tactile sensor application apparatus using the tactile sensor.

BACKGROUND ART

Almost every conventional pressure and position detection sensor detects a pressure distribution, and scans sensors or electrodes arranged on an X-Y matrix to detect the pressure distribution and calculates positions of pressure (see, for example, patent documents 1 and 2). However, in order to X-Y scan all the positions that are subjected to pressures, it takes time to calculate a center of gravity location of the pressures, an area of the pressures and an average pressure that are necessary information. For example, in the case where a sensor of 50×50 mm with a resolution of 1 mm is scanned even at 100 MHz, it takes 25μsec per element. Moreover, hard wires (2500 lines) to these scanning lines (50×50) become huge wiring as the sensor becomes a large one, which has become application hindrances.

Moreover, although pressure and position detection sensors that each combine a pressure sensor and X-Y coordinate detecting means to demonstrate similar functions are proposed by patent documents 3 to 8, since each detects pressure and position information by a combination of two or more sheets of functional materials, when position information of a pressing can be detected accurately, it is impossible to detect pressure information at that position. Conversely, when pressure information can be detected accurately, that position information becomes inaccurate, and therefore there is a shortcoming that both of a pressure and a center of gravity coordinates of the pressure cannot be detected accurately.

Furthermore, although pressure and position detection sensors each of which combines pressure sensitive conductive rubber or a piezoelectric composite material and a resistor to detect pressure coordinates have been proposed, each one cannot provide precision. In addition, they are not for obtaining a pressure and a contact area. Therefore, they are insufficient as a pressure and position detection sensor or a tactile sensor (see, for example, patent documents 9 to 11).

Patent document 1: Japanese Unexamined Patent Publication No. JP-A 10-178688 (1998)

Patent document 2: Japanese Patent Publication No. JP-B 7-58233 (1995)

Patent document 3: Japanese Unexamined Patent Publication No. JP-A 59-178301 (1984)

Patent document 4: Japanese Patent Publication No. JP-B 60-35602 (1985)

Patent document 5: Japanese Patent Publication No. JP-B 61-32601 (1986)

Patent document 6: Japanese Patent Publication No. JP-B 60-37401(1985)

Patent document 7: Japanese Unexamined Patent Publication No. JP-A 61-208533 (1986)

Patent document 8: Japanese Unexamined Patent Publication No. JP-A 05-61592 (1993)

Patent document 9: Japanese Unexamined Patent Publication No. JP-A 59-110595 (1984)

Patent document 10: Japanese Unexamined Patent Publication No. JP-A 60-71194 (1985)

Patent document 11: Japanese Unexamined Patent Publication No. JP-A 61-47501 (1986)

DISCLOSURE OF INVENTION

Problems to be Solved by the Invention

Recent years a large number of robotic systems that bears animal forms as well as being humanoid types are provided. Such robotic systems include a large number of systems that are required to act in real time in response to a stimulus caused by a contact from the outside. In order to balance a body of a two-legged robot of recent years at the time of walking, it is practiced that a pressure sensor is installed onto soles of foot and a delicate change of balance is detected in real time in advance and is used for controlling. Moreover, in order to detect a tactile sense of fingers of hand, real time control, such as pressure control when a robot has an object in its hand and detection of pressure variation when an object slips, is considered to be necessary. For this purpose, practically a large number of pressure sensors are arranged and pieces of sensor information are processed simultaneously by parallel processing or similar process is conducted. However, hard wires of the large number of pressure sensors have become an obstacle of apparatus.

Moreover, if a pressure of a human body excessively biased, for example, in a chair for care and a bed for care, it may cause something wrong in the human body. There is a case where a person who needs care cannot avoid the situation by oneself, and it may become a cause of bedsore, etc. Moreover, if a position of a passenger sitting on a seat of an automobile for which safety is required is shifted, it becomes difficult to blow an airbag open accurately to the center of the passenger at the time of an accident.

In these usage, the tactile sensor and the pressure and position detection sensor that can detect necessary minimum pieces of information (a center of gravity location of the pressure, a pressure contact area, and an average pressure quantity) even if a pressure distribution is not known accurately and that can detect pressure and its position with a reduced number of hard wires are desired.

The present invention intends to detect a variation of the pressing in real time in view of the above-mentioned problems. Moreover, the present invention makes it possible for a sensor to detect the variation of the pressing with a simple configuration and a reduced number of hard wires, to attain improvement of reliability and curtailment of the cost, and enables the sensor to obtain information accurately.

Means for Solving Problems

The technical means of the present invention to solve these technical problems including: a pressure sensitive resistance sheet that is a sheet having resistance in an X direction and in a Y direction along a sheet plane and that has resistance in a Z direction coinciding with a thickness direction of the sheet, the resistance in the Z direction varying in response to a pressing in the thickness direction, characterized in that at least one pair of electrode parts that is for passing a current in at least one of resistance in the X direction and resistance in the Y direction is provided in the periphery of this pressure sensitive resistance sheet and at least one pair of electric conductors for passing a current in the Z direction is provided on a surface of the pressure sensitive resistance sheet.

Moreover, other technical means of the present invention is characterized in that, when a current is made to flow in any one of the electrode parts and the electric conductors and the current is taken out from the remaining electrode parts or the electric conductors, a contact pressure and at least one of a contact position in the X direction and a contact position in the Y direction are intended to be obtained from a combination of a voltage of the above-mentioned at least one pair of electrode parts and a voltage of the above-mentioned at least one pair of electric conductors.

Furthermore, further another technical means of the present invention is characterized in that, when a current is made to flow in any one of the electrode parts and the electric conductors and the current is taken out from the remaining electrode parts or the electric conductors, it is so configured that a voltage difference of the voltage of the above-mentioned at least one pair of electrode parts between before contacting the tactile sensor and at the time of contacting the tactile sensor may be corrected to a value that corresponds to the obtained contact pressure and the contact position, and thereby at least one of the contact length in the X direction and the contact length in the Y direction may be obtained.

In addition, as other technical means, the apparatus may be such that the apparatus has a pair of first electrode parts for passing a current through the pressure sensitive resistance sheet in the X direction and a pair of second electrode parts for passing a current therethrough in the Y direction; at four corners of the pressure sensitive resistance sheet, a first electrode, a second electrode, a third electrode, and a fourth electrode are provided, respectively; one first electrode part of the one pair of the first electrode parts includes the first electrode and the third electrode and the other first electrode part thereof includes the second electrode and the fourth electrode; one second electrode part of the one pair of the second electrode parts includes the first electrode and the second electrode and the other second electrode part thereof includes the third electrode and the fourth electrode; the each electrode is fixed on the pressure sensitive resistance sheet by pressure welding with a predetermined pressure or more; and electric conductors for passing a current in the Z direction are held on a surface of the pressure sensitive resistance sheet using spacer at predetermined intervals.

Moreover, other technical means of the present invention is in that the apparatus has a pressure sensitive resistance sheet that is a sheet having resistance in a direction along the sheet plane and whose resistance in the thickness direction varies in response to the pressing in the thickness direction, wherein a current is made to flow in the pressure sensitive resistance sheet in order to obtain at least two of the contact pressure, the contact position, and the contact length of the pressure sensitive resistance sheet, and the pressure sensitive resistance sheet is made up of a film having a surface resistance ranging from a few kilo ohms to a few tens of mega ohms. In this case, for example, a current may be made to flow in a pressure sensitive resistance sheet in a direction along that sheet plane, and/or in the thickness direction.

Furthermore, other technical means of the present invention is such configuration in that the pressure sensitive resistance sheet is made up of a film having a surface resistance ranging from a few kilo ohms to a few tens of mega ohms.

Still moreover, other technical means of the present invention has a controlled apparatus in which the tactile sensor is installed, a power supply for generating a potential gradient in the pressure sensitive resistance sheet, and an A/D converter for converting an output voltage of the electrode parts and the one pair of the electric conductors into a digital signal, and a control unit that obtains at least two of the contact pressure to the tactile sensor, the contact position, and the contact length in the X direction and/or in the Y direction and controls the controlled apparatus 1 based on these obtained contact pressure, the contact position, and the contact length.

Effect of the Invention

According to the present invention, the variation of the pressing can be detected in real time by detecting only the center of gravity coordinates of the pressing, a value of pressure, and its contact length, not detecting the pressure distribution of the pressing. Moreover, since the apparatus is realized with an analog type coordinate sensing device and an analog contact pressure detection sensor disposed on the same plane, as compared with conventional digital X-Y matrix sensors, the configuration is simple and detection becomes possible with a fewer hard wires, and therefore improvement of reliability and curtailment of cost can be attained. Moreover, since unlike conventional analog type apparatuses, the invention can detect information on the same plane, the information can be obtained accurately.

BRIEF DESCRIPTION OF DRAWINGS

FIG. 13 is a diagram showing an order of changeover of a circuit changing switch that shows another embodiment.

DESCRIPTION OF REFERENCE NUMERALS

Figure 1:
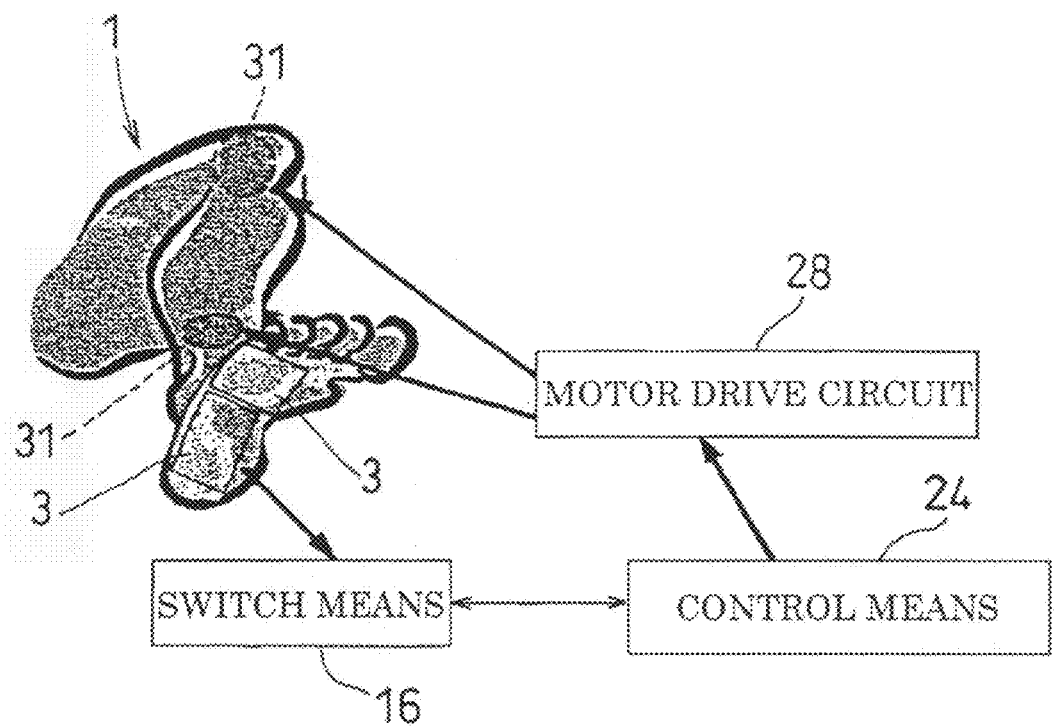
FIG. 1 is a perspective view of a leg part of a robot that shows one embodiment of the present invention.

1 Robot (Controlled apparatus)
3 Tactile sensor

4 Pressure sensitive resistance sheet
5 Conductive film (Electric conductor)
6 Conductive film (Electric conductor)
9 First electrode part
10 First electrode part
11 Second electrode part
12 Second electrode part
27 Control unit
30 External controller

BEST MODE FOR CARRYING OUT THE INVENTION

Figure 2:
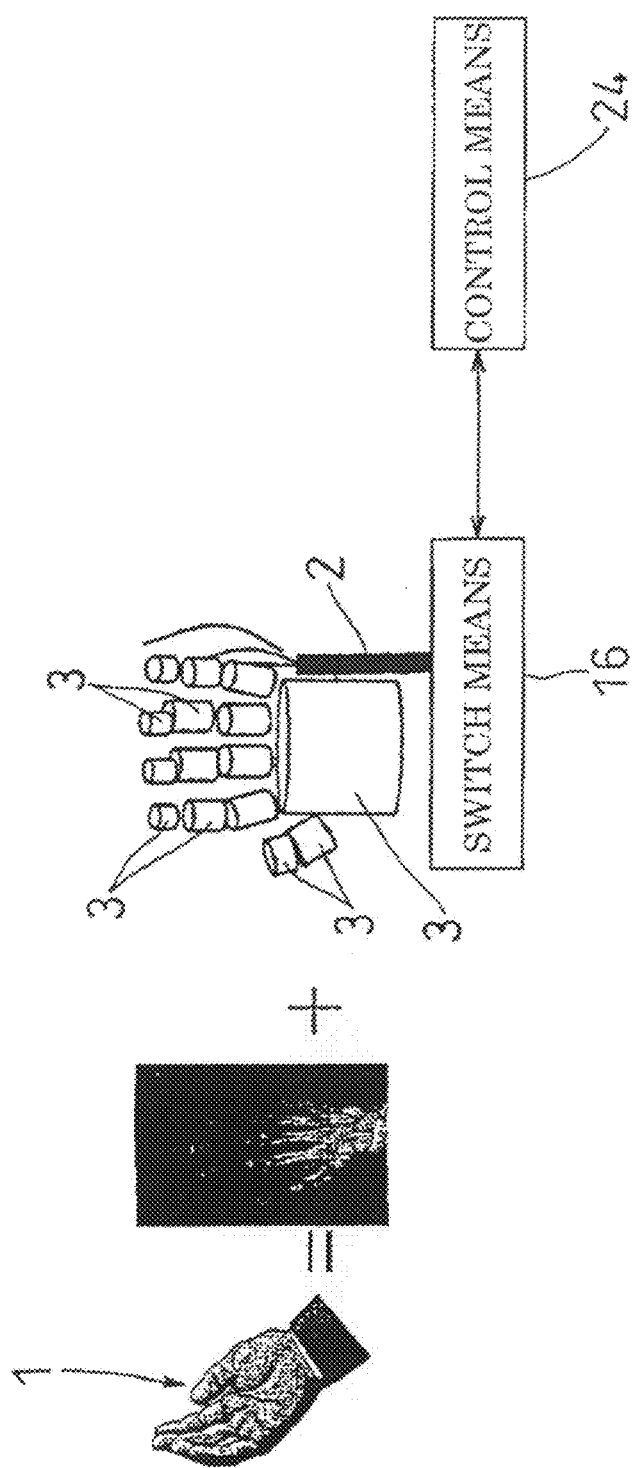
FIG. 2 is a perspective view of a hand part of the robot that shows one embodiment of the present invention.

Hereafter, embodiments of the present invention will be described referring to the drawings. FIGS. 1 and 2 show one embodiment in which the present invention is applied to a palm or a hand of a robot (controlled apparatus) 1. In the embodiment, a tactile sensor 3 that is built in a unit is installed onto joints of a sole, fingers, or a palm that are skeleton of a robot 1, being fitting to these parts. In the present embodiment, as shown in FIG. 1, the two tactile sensors 3 are installed onto the sole of the robot 1, and as shown in FIG. 2, the fourteen tactile sensors 3 are installed onto the fingers of the hand and each one tactile sensor is installed onto the palm of the hand and to the back of the hand, respectively. Since these tactile sensors 3 are arranged being fitted to joints of the hand and the sole of the foot, the joints can be operated freely and magnitudes of pressures thereof and their areas and a center of gravity location of the pressure can be obtained with a precision of mm or less in real time. In the case where the tactile sensor 3 is installed onto the sole, it is easy to detect a variation of pressure at the time of walking; in the case where it is installed onto the fingers of the hand, it is easy to detect a variation of pressure at the time of grasping a thing, slip, etc. As described later, since signal wires 2 coming out from the tactile sensor are as few as four to six for the one tactile sensor 3, and therefore it is very rare that the hard wires coming out therefrom gives obstacles and hinders a delicate operation of the fingers of the robot hand, such as grasping, touching, etc.

Figure 3:
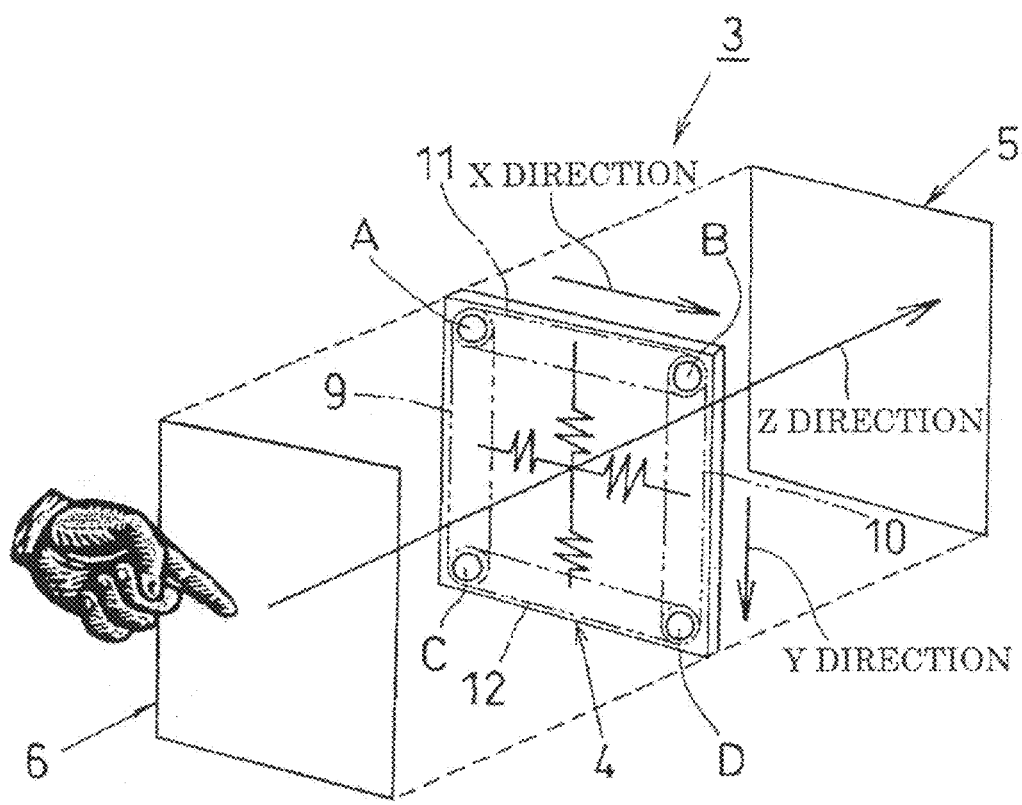
FIG. 3 is an exploded perspective view of a tactile sensor that shows one embodiment of the present invention.
Figure 4:
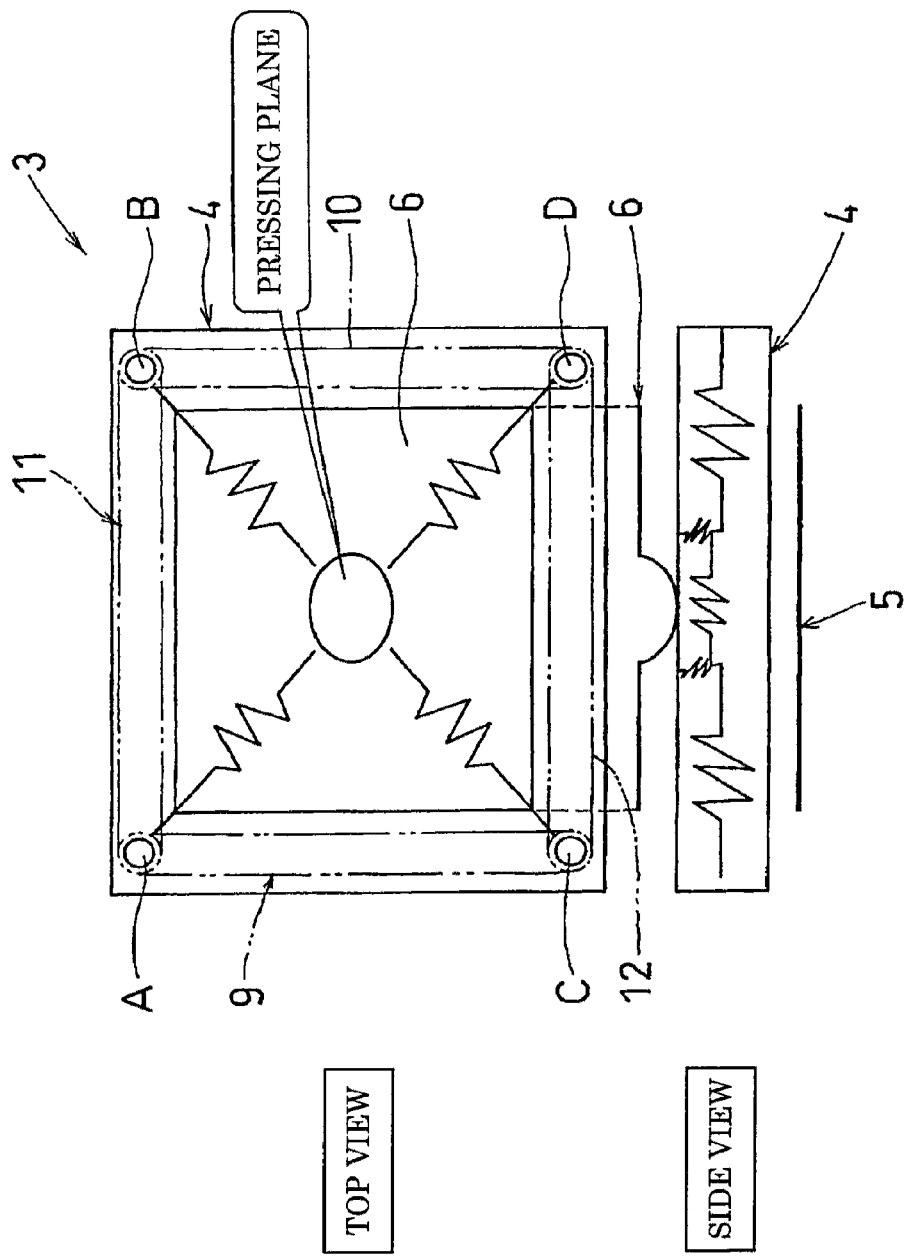
FIG. 4 is a conceptual diagram showing one example of how to detect a contact area of the tactile sensor that shows one embodiment of the present invention.

Next, a structure of the tactile sensor 3 will be explained in detail. FIG. 3 is a developed view of the tactile sensor 3 disposed on one of the sole, the fingers, or the palm shown in FIGS. 1 and 2 (in FIG. 2, what this is wound around the finger is used). FIG. 4 is a schematic view of the tactile sensor 3, showing it in the top view and the side view. In FIGS. 3 and 4, the tactile sensor 3 has a pressure sensitive resistance sheet 4 and a pair of conductive films (electric conductors) 5, 6 arranged so that the pressure sensitive resistance sheet 4 may be sandwiched from the both sides of the thickness direction.

The pressure sensitive resistance sheet 4 is a sheet that has resistance in an X direction and in a Y direction along the sheet plane, and that has resistance in a Z direction coinciding with a thickness direction of the sheet and also pressure sensitivity in the thickness direction, being formed to vary the resistance in the Z direction in response to pressing in the thickness direction. In the present embodiment, the pressure sensitive resistance sheet 4 is made up of a sheet in which, for example, carbon is mixed in polyethylene so that it has a surface resistance of about $10^4$ to $10^8$.

The sheet having a surface resistance of about $10^4$ to $10^8$ is carbon-mixed polyethylene film 100 μm thick that can be usually obtained on the market, and is frequently used in conductive bags etc. for protecting electronic boards that carry semiconductor IC's and electronic parts thereon from static electricity, usually being commercially available. Although the sheet having a surface resistance of about $10^4$ to $10^8$ was used, since pressure sensitive resistance sheets used in various applications differ in shape, resistance between the electrodes may also differ largely. In actual control circuits, it is preferable that the resistance between the electrodes and the pressure sensitive resistance are set optimally so that they may not affect circuit input impedance as an input of the controlling means and the switching means. Therefore, according to various applications, sheets of surface resistance ranging from a few kilo ohms to a few tens of mega ohms can be used. However, for the surface resistance values over this value, the resistance value in the X direction or in the Y direction becomes large, detection of contact coordinates becomes difficult, while in the surface resistance values not more than this value, there is a case where pressure sensitive characteristic is insufficient, which hinders the detection.

One pair of first electrode parts 9, 10 for passing a current in the X direction and one pair of second electrode parts 11, 12 for passing a current in the Y direction are provided in the peripheral part of the pressure sensitive resistance sheet 4. For example, the one pair of the first electrode parts 9, 10 is specified to be electrode parts for passing a current in resistance in the X direction of the pressure sensitive resistance sheet 4; the one pair of the second electrode parts 9, 10 is specified to be electrode parts for passing a current in resistance in the Y direction of the pressure sensitive resistance sheet 4.

The pressure sensitive resistance sheet 4 is formed in the shape of a rectangle, and in four corner parts of this pressure sensitive resistance sheet 4, a first electrode A, a second electrode B, a third electrode C, and a fourth electrode D are formed, respectively. The one first electrode part 9 includes the first electrode A and the third electrode C. The other first electrode part 10 includes the second electrode B and the fourth electrode D. The one second electrode part 11 includes the first electrode A and the second electrode B. The other second electrode part 12 includes the third electrode C and the fourth electrode D. The first electrode A, the second electrode B, the third electrode C, and the fourth electrode D are constructed, for example, attaching copper foil on the pressure sensitive resistance sheet 4.

The one pair of the conductive films 5, 6 is provided on one pair of surfaces corresponding to the thickness direction of the pressure sensitive resistance sheet 4, respectively. For example, the one pair of the conductive films 5, 6 is specified to be conductors (the third electrode part) for passing a current in resistance in the Z direction of the pressure sensitive resistance sheet 4. The conductive films 5, 6 are films whose surfaces facing the pressure sensitive resistance sheet 4 have conductivity, respectively. It may be made up of aluminum PET (Polyethylene terephthalate) obtained by depositing aluminum on a surface of PET, or may be made up of a FPC (Flexible Printed Circuit board) obtained by coating a conductive film on PI (Polyimide). This one pair of conductive films 5, 6 is formed in a rectangular shape, respectively, corresponding to the pressure sensitive resistance sheet 4, and the conductive films 5, 6 take forms of one pair of third electrode parts in order to pass a current through the pressure sensitive resistance sheet 4 in the Z direction. Incidentally, in a case where one pair of conductive films 5, 6 is used as one pair of the third electrode parts, hard wires from the power supply etc. may be configured to be connected to the one pair of conductive films 5, 6 directly, or electrodes made by attaching copper foil on the one pair of conductive films 5, 6 is provided thereon and hard wires from the power supply etc. may be configured to be connected to these electrodes.

Next, a principle whereby detection of the contact pressure (sensing of a pressure) and detection of a contact position (position coordinates) are performed using the pressure sensitive resistance sheet 4 will be explained.

The pressure sensitive resistance sheet 4 shows variation in resistance to the pressing force in the thickness direction. For example, when a load of 1 N (Newton) is applied to an area with 4 mm in diameter on the pressure sensitive resistance sheet 4, it shows a resistance of a few tens kilo ohms, whereas in the presence of a load of 100 N, it becomes a few tens ohms. What has the same function is the well-known pressure sensitive conductive rubber. The pressure sensitive conductive rubber is a composite material in which silicone rubber is combined with metallic or carbon particle. It is a pressure conductive rubber that exhibits variation in resistance from an insulating state to a conductive state and has conductivity in response to a pressure stimulus because internal metallic particles contact one another. A function in the thickness direction is the same as the pressure sensitive resistance sheet 4 that is mixed with the above-mentioned carbon and is used in the invention. However, since the pressure conductive rubber includes a rubber with high insulating performance and a metallic particles with high conductivity, as has been used as anisotropic conductivity connector in which metallic particles are arranged in the thickness direction of the silicone rubber film in order to connect electrodes on a liquid crystal glass panel and an FFC cable to be connected to the outside, it exhibits conductivity with respect to applied pressure to the thickness direction but exhibits high insulating performance in a X-Y plane in the surrounding area of a pressure applied point. Conventionally, in order to detect an X-Y coordinate position, as described above, it is carried out by being combined with other components.

On the other hand, the pressure sensitive resistance sheet 4 that is used in the invention and is made up of a polyethylene film with carbon mixed therein and has predetermined resistance even in the X-Y plane, compared with conventional pressure sensitive conductive rubbers. Therefore, as long as a predetermined resistance value can be obtained even in the X-Y plane, there is no problem in using rubber for a base material as the pressure sensitive resistance sheet 4 or in using other pressure sensitive materials.

Although the pressure sensitive resistance sheet 4 is sandwiched by the two sheets of the conductive films 5, 6 whose conductive planes are in touch with the two sheets of the conductive films 5, 6. It is referable that the spacer exists between the two sheets of the conductive films 5, 6 and preferably the spacer is designed such that, when no pressing is applied, a space between the two sheets of the conductive films 5, 6 is insulated or has two times higher resistance than a resistance value of the pressure sensitive resistance sheet 4 in the thickness direction (the Z direction).

A gap may be made by inserting film spacer of thickness from a few μm to a few tens of μm, as spacer, into a left and right both ends, or the gap may be made using micro spacer of spherical resin beads in size from a few μm to a few tens of μm that are used in the touch panel and the liquid crystal panel. The pressure sensitive resistance sheet 4 is so made that, by pressing of the conductive films 5, 6, the conductive plane of the conductive films 5, 6 may contact the pressure sensitive resistance sheet 4 at the pressing position. When securing the gap with the micro spacer, the pressure detection initiating sensitivity to the pressing varies with the distribution density of the micro spacer. In the case where the density is large, when the pressing is not large, the conductive plane of the conductive films 5, 6 does not contact the pressure sensitive resistance sheet 4. Moreover, since it is detectable by a little pressing, in the case where the density is small, the density of the micro spacer can be chosen according to a use. Naturally, since this is affected by the thicknesses of the conductive films 5, 6 and rigidity thereof, the pressure detection initiating sensitivity must be determined by conditions of these conductive films 5, 6 and the micro spacer.

Now, using the thus configured tactile sensor 3, a basic operation for detecting input information will be explained. As a contact pressure detection means adapted to detect contact pressure, the conductive film 5, the pressure sensitive resistance sheet 4, and the conductive film 6 are used. A plane where a conductive plane of the conductive film 6 and the pressure sensitive resistance sheet 4 contact is defined as a tactile sensor area, and a plane where a conductive plane in which the conductive film 5 and the conductive film 6 face each other and the pressure sensitive resistance sheet 4 contact each other is defined as a tactile pressure sensor area. Therefore, the electric conduction area of the conductive film 6 may not necessarily be the same as the electric conduction area of the conductive film 5. A constant current is made to flow between this one pair of conductive films 5, 6 (one pair of the third electrode parts). As described above, by giving a pressure to the conductive film 6, a pressure is added to the pressure sensitive resistance sheet 4, and the resistance value in the Z direction varies. Therefore, in the case where a current flowing in the pair of the conductive films 5, 6 is kept at a constant, an applied pressure force (contact pressure) can be obtained from a voltage Vz between the conductive films 5, 6 (the third electrode part). That is, when a current is made to flow from the conductive film 5 and the current is taken out from the conductive film 6, a contact pressure can be obtained from a difference (combination) between a voltage V5 of the conductive film 5 and a voltage V6 of the conductive film 6.

Figure 5:
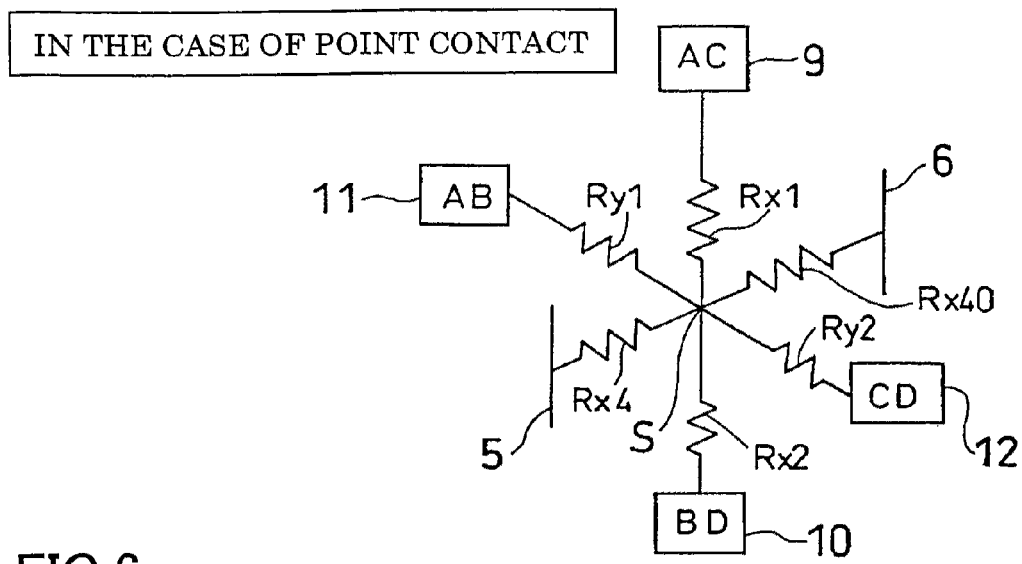
FIG. 5 is an equivalent circuit of a pressure sensitive resistance sheet in a case of conducting point contact to the tactile sensor that shows one embodiment of the present invention.

Next, detection means adapted to detect the contact position (X, Y coordinates by contact) will be explained. A voltage Vx0 is added to the first electrode A and the third electrode C (the first electrode part 9) of the pressure sensitive resistance sheet 4, and the second electrode B and the fourth electrode D (the first electrode part 10) are set to GND. FIG. 5 shows an equivalent circuit of the pressure sensitive resistance sheet 4 in the case of point contact. As shown in FIG. 5, when a certain coordinate position of the conductive film 6 is pressed down, the electric conduction plane of the conductive film 6 will contact the pressure sensitive resistance sheet 4. Consider that a point S with a distance X1 in the X direction from a position of the second electrode B and the fourth electrode D (the first electrode part 10) is contacted. A voltage Vzx of the conductive film 6 (the third electrode part) is expressed by $Vzx=X1/(X1+X2)*Vx0$.

Here, X2 denotes a distance from the positions of the first electrode A and the third electrode C (the first electrode part 9) to a contact point S.

Therefore, when a voltage Vx0 is impressed between the one pair of the first electrode parts 9, 10 and a current in the X direction is made to flow in the pressure sensitive resistance sheet 4, the voltage Vzx between one first electrode part 9 and one conductive film 6 is detected, and a contact position in the X direction can be obtained from a relationship of this detected voltage Vzx and the impressed voltage Vx0. That is, when a current is made to flow from the first electrode part 9 and the current is taken out from the first electrode part 10, the contact position in the X direction can be obtained from a difference (combination) between a voltage V9 of the first electrode part 9 and a voltage V10 of the first electrode part 10 and a difference (combination) between the voltage V9 of the first electrode part 9 and the voltage V6 of the conductive film 6.

Similarly, consider that a voltage Vy0 is added to the first electrode A and the second electrode B (the second electrode part 11), and the third electrode C and the fourth electrode D (the second electrode part 12) are set to GND. The voltage is expressed by $Vzy=Y1/(Y1+Y2)*Vy0$.

Here, Y1 denotes a distance from the positions of the third electrode C and the second electrode D (the second electrode part 12) to the contact point S, and Y2 denotes a distance from the positions of the first electrode A and the second electrode B (the second electrode part 11) to the contact point S.

Therefore, when the voltage Vy0 is impressed between a pair of the second electrode parts 11, 12 and a current in the Y direction is made to flow in the pressure sensitive resistance sheet 4, the voltage Vzy between one second electrode part 11 and one electric conductive film 6 is detected, and from a relationship of this detected voltage Vzy and the impressed voltage Vy0, the contact position in the Y direction can be obtained. That is, when a current is made to flow from the second electrode part 11 and the current is taken out from the second electrode part 12, the contact position in the Y direction can be obtained from a difference (combination) between the voltage V11 of the second electrode part 11 and the voltage V12 of the second electrode part 12 and a difference (combination) between the voltage V11 of the one second electrode part 11 and the voltage V6 of the one conductive film 6.

Moreover, the position coordinates can be obtained by making a current flow from the conductive film 6 at the contact position to the electrode part of the pressure sensitive resistance sheet 4 and detecting the current that flows to the electrode parts arranged in the pressure sensitive resistance sheet 4. At this time, a current having a value in inverse proportion to a distance to the contact point begins to flow in the four corner parts.

Figure 6:
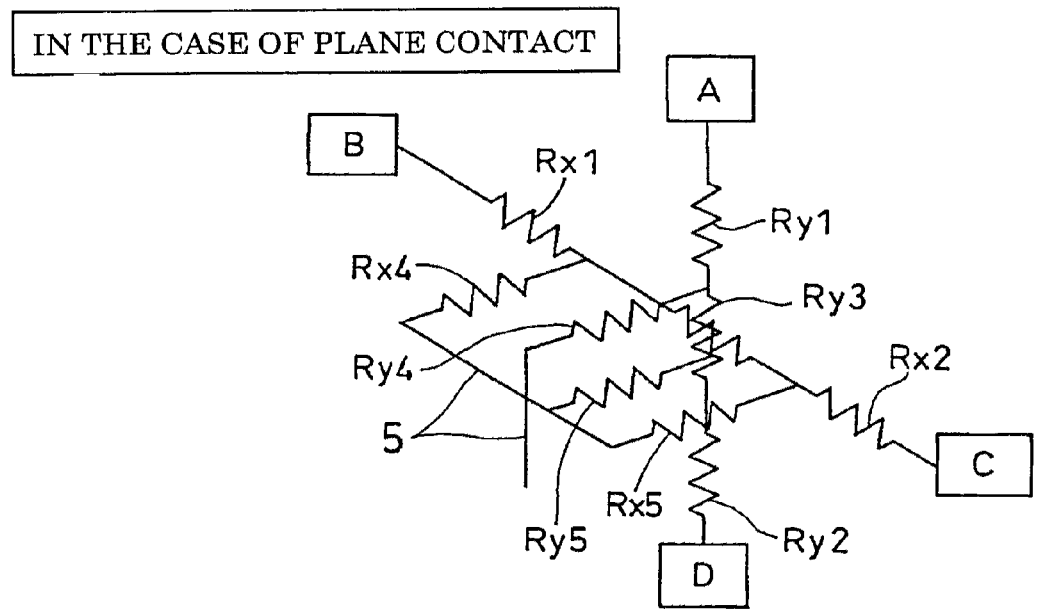
FIG. 6 is an equivalent circuit of the pressure sensitive resistance sheet in a case of conducting plane contact to the tactile sensor that shows one embodiment of the present invention.
Figure 7:
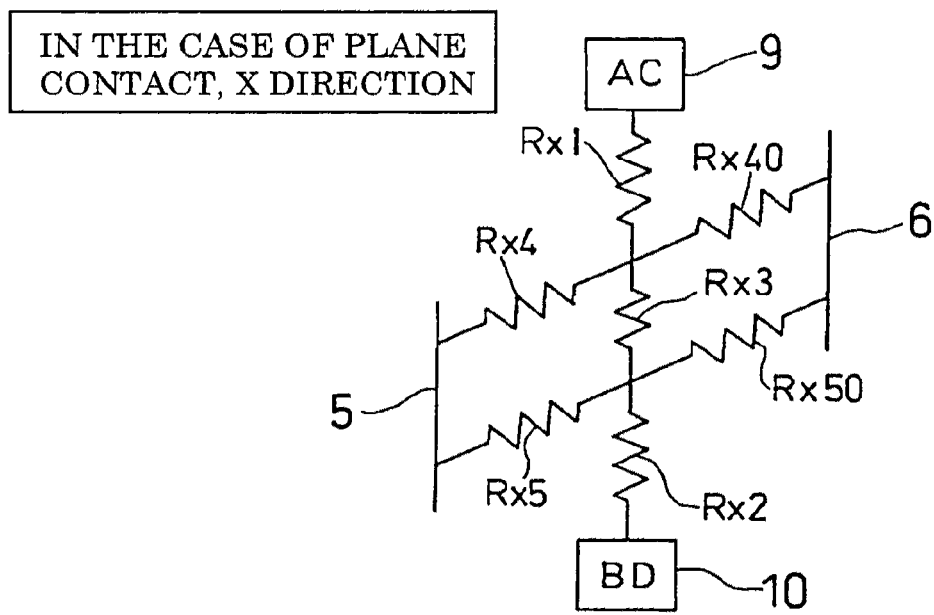
FIG. 7 is an equivalent circuit in an X direction of the pressure sensitive resistance sheet in the case of conducting plane contact to the tactile sensor that shows one embodiment of the present invention.
Figure 8:
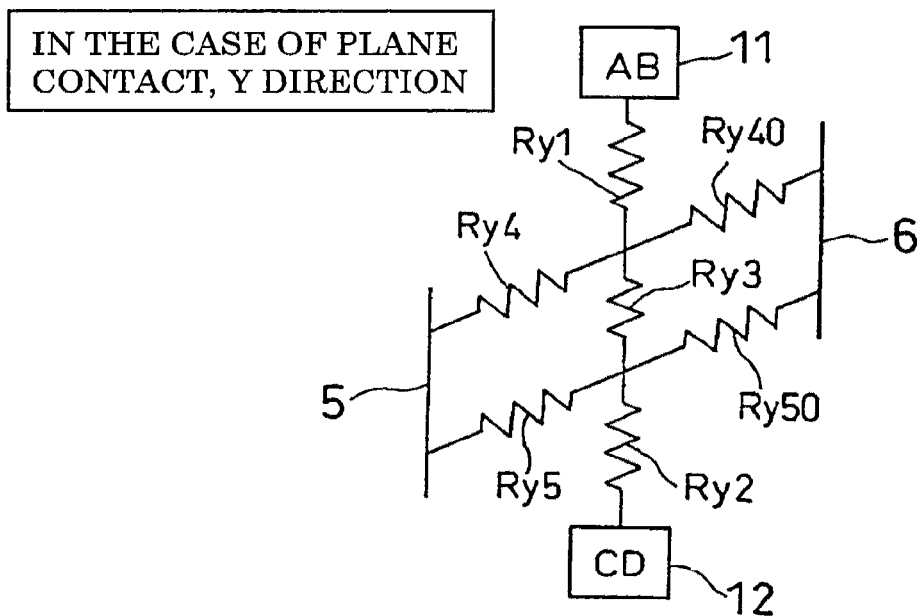
FIG. 8 is an equivalent circuit in a Y direction of the pressure sensitive resistance sheet in the case of conducting plane contact to the tactile sensor that shows one embodiment of the present invention.

FIGS. 6 to 8 show the equivalent circuits in a case of conducting plane contact, and FIG. 6 shows an equivalent circuit of resistance in the X direction and in the Y direction in a case of conducting plane contact. FIG. 7 shows an equivalent circuit when the resistance in the Y direction in the case of conducting plane contact is omitted and only resistance in the X direction is rendered; FIG. 8 shows an equivalent circuit when the resistance in the X direction in a case of conducting plane contact is omitted and only resistance in the Y direction is rendered. As shown in FIGS. 6 to 8, the contact coordinates can be obtained by a ratio of Vzx/Vx0 and a ratio of Vzy/Vy0, as in the case of FIG. 5. Since the voltage Vzx is a voltage corresponding to a ratio of pressure sensitive resistance Rx4 and pressure sensitive resistance Rx5 and the voltage Vzy is a voltage corresponding to a ratio of pressure sensitive resistance Ry4 and pressure sensitive resistance Ry5, the voltage V6 detected by the conductive film 6 is not for the center of the contact area, and a voltage at a position in proportion to the pressure distribution of the pressing will be outputted. Especially in the present invention, since the position coordinates and pressure information on the same plane can be taken in, the detection can be performed accurately.

Usually, in the case where there is an area in the contact surface, an error occurs in detecting the contact coordinate position that does not accompany contact pressure information. Conventionally (for example, Japanese Examined Patent Publication JP-B2 3055448), in order to solve the problem, accurate contact coordinates are obtained from a change depending on the size of the contact surface. Since distribution information of the contact pressure is not taken in into the method, if correction is performed in an contacted area for which pressure information is not taken in, for example, in a case where the contact pressure is large at one edge of the contact surface, there is the possibility that an error of the center position of the contact becomes large conversely. In the present invention, since from one sheet of pressure sensitive resistance sheet 4, X-Y coordinates at the contact position are obtained by a ratio that corresponds to pressure forces in the plane, the X-Y coordinates can be obtained more accurately.

Next, as means adapted to detect a contact length from a contact peripheral pressure, the pressure sensitive resistance sheet 4 and the conductive film 6 are used. First, with a constant current added between the first electrode A and the third electrode C of the pressure sensitive resistance sheet 4 (one first electrode part 9) and the second electrode B and the fourth electrode D (the other first electrode part 10) before being given a contact pressure, a voltage Vx0 between the one pair of the first electrode parts 9, 10 is detected. Next, a constant current is added between the first electrode A and the second electrode B (one second electrode part 11) of the pressure sensitive resistance sheet 4 and between the third electrode C and the fourth electrode D (the other second electrode part 12), and the voltage Vy0 between the one pair of the second electrode parts 11, 12 is detected. When a contact pressure is given with a certain area at a certain position of the pressure sensitive resistance sheet 4 with an intermediary of the conductive film 6, a constant current that is made to flow between the one pair of the first electrode parts 9, 10 and the one pair of the second electrode parts 11, 12 flows from the pressure sensitive resistance sheet 4 to the conductive films 5, 6 on the contact surface, and voltages Vx, Vy between the one pair of the first electrode parts 9, 10 and between the one pair of the second electrode parts 11, 12 decrease, respectively. The amount of change Vx0−Vx in this X direction and the amount of change Vy0−Vy in the Y direction can be defined as a contact area that corresponds to the contact pressure. If the contact surface becomes large, the current passing through the conductive films 5, 6 will increase, and a voltage Vx between the first electrode parts 9, 10 and a voltage Vy between the second electrode parts 11, 12 will decrease.

Explaining this using an equivalent circuit in FIGS. 5 to 8, FIGS. 5 to 8 show resistance of the parts when the conductive film 6 and the pressure sensitive resistance sheet 4 are given pressures. FIG. 5 is an equivalent circuit in the case of point contact. There is no variation in resistance between the first electrode pairs 9, 10 and, or between one pair of the second electrode parts 11, 12 due to the contact.

FIGS. 6 to 8 are equivalent circuits in the case of conducting plane contact. Although the equivalent circuits are expressed by positions of the contact surface and a resistance distribution of the pressure sensitive resistance sheet 4 at the positions, FIGS. 6 to 8 are equivalent circuits each of which is shown by a simple model. The current between the one pair of the first electrode parts 9, 10 flows as shown in FIGS. 6 and 7. That is, at positions other than the contact surface, the current flows in resistance Rx1 of the pressure sensitive resistance sheet 4; and in the contact surface, at position coordinates of an edge part of the contact surface where the applied pressure is large, the current flows in the conductive film 6 through the pressure sensitive resistance Rx4 and the current flows to the conductive film 5 through pressure sensitive resistance Rx40. Total sum of the current that flows in the pressure sensitive resistance Rx5 and a pressure sensitive resistance Rx50 at the position coordinates of other edge part of the contact surface where the applied pressure is large and the current that flows in pressure sensitive resistance Rx3 of the pressure sensitive resistance sheet 4 will flow in pressure sensitive resistance Rx2 of the pressure sensitive resistance sheet 4. Since these currents flow in the conductive films 5, 6 through the pressure sensitive resistance Rx4, the pressure sensitive resistance Rx40, the pressure sensitive resistance Rx5, and the pressure sensitive resistance Rx50 at the position coordinates of the edge part of the contact surface, the detected amount of voltage change V0x-Vx is not simply proportional to the contact area but is also affected by a pressure of an outer peripheral where the contact pressure contacts. The value will determine a threshold when detecting the contact area. The value will be determined by a current flowing so that the resistance between the electrodes may become the smallest.

Figure 9:
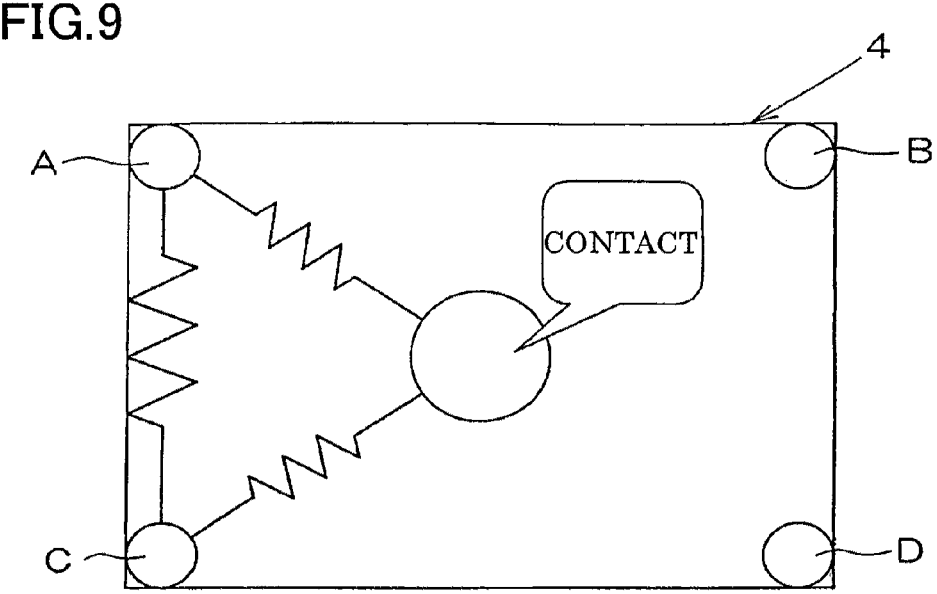
FIG. 9 is an equivalent circuit in the case where a contact position to the tactile sensor that shows one embodiment of the present invention is near the center.
Figure 10:
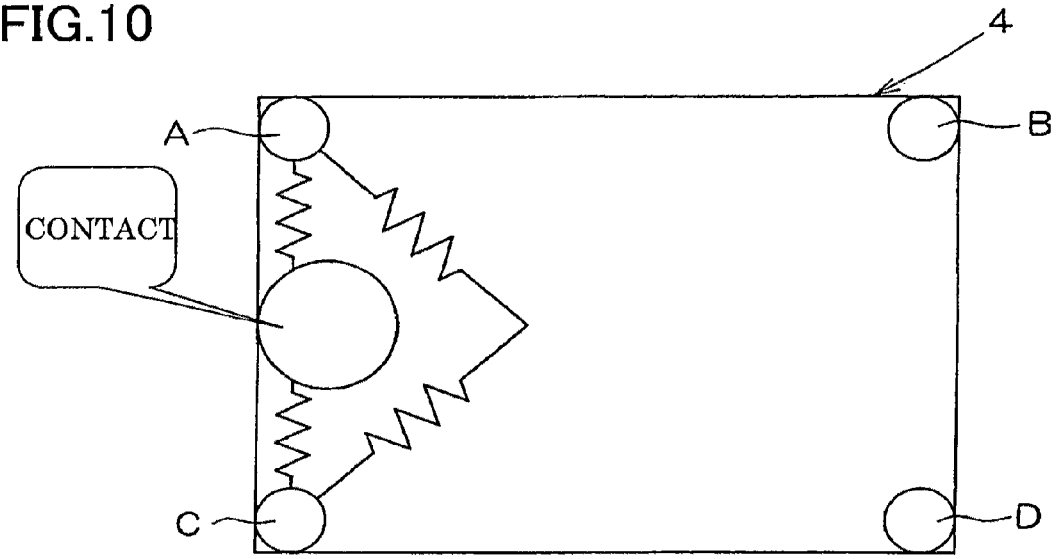
FIG. 10 is an equivalent circuit in the case where the contact position to the tactile sensor that shows one embodiment of the present invention is in the periphery or its surrounding.

Moreover, FIG. 9 shows an equivalent resistance between the electrodes A, C and the contact position when the contact position is located near the center of the tactile sensor 3; FIG. 10 shows an equivalent resistance between the electrodes A, C and the contact position when the contact position is located near the periphery of the tactile sensor 3. Since the current flows so that a resistance becomes smallest between the electrodes, in the case where the contact position deviates from a shortest distance connecting the contact position and the electrode, variation of resistance between the electrode becomes smaller even when the contact area is the same, as shown in FIGS. 9 and 10. Therefore, the equivalent resistance needs to be corrected depending on the contact coordinates.

Moreover, although regarding the contact length, a current was made to flow at the electrode parts 9, 10, 11 and 12 and its variation was detected. The contact length may be calculated by making a current flow from the electric conductor 5 or the electric conductor 6, detecting a variation of the voltage at the electrode parts 9, 10, 11 and 12, and referring to combinations of the voltages to obtain already detected contact pressure and contact coordinates.

Since in the present invention, pressures surrounding the contact on the same plane can be taken in, a high-precision value for the detected contact area can be obtained. Incidentally, in a case where the contact area is small, since the pressure sensitive resistance Rx3 and pressure sensitive resistance Ry3 shown in FIGS. 6 to 8 are small, the current leaking into the conductive films 5, 6 decreases, and the contact area is detected smaller. These values may be utilized after by simple correction, or a load given on the contact surface may be corrected by combining this with the previously detected pressure value.

Although in the foregoing, an electrode configuration in a case of pressure detection and that at the time of coordinate detection were set identical, and the control methods were set to be the same system, the pressures were detected using a control unit 27 in common by performing changeover with the switch means 16, an the coordinates were detected in the X direction and in the Y direction, separately, and thereby the contact length was obtained. However, the position coordinates in the X direction and in the Y direction can be detected simultaneously by a control method in which the pressure is detected using a current flowing in the electrode parts 9, 10, 11 and 12 (electrode A, B, C and D) arranged on the pressure sensitive resistance sheet 4, by making a current flow in the electrode parts 9, 10, 11 and 12 (electrode A, B, C and D) and taking out the current from the electric conductor 5.

Although in the above-mentioned embodiment, the X-Y coordinate positions are obtained, the sensor may be configured to obtain only the X coordinate or the Y coordinate with sensor electrodes of a simplified structure. To sum up, what is necessary in the sensor is that it has a pressure sensitive resistance sheet 4 that has resistance in a direction along the sheet plane, that has resistance in the thickness direction of the sheet, and whose resistance in the thickness direction varies in response to the pressing in the thickness direction, and a current is made to flow in the pressure sensitive resistance sheet 4 in a direction along the sheet plane and/or in the thickness direction in order to obtain at least two of the contact pressure to the pressure sensitive resistance sheet 4, the contact position thereof, and the contact length thereof.

Next, an operation of the tactile sensor of the present invention and a control of the robot 1 using the tactile sensor will be explained in detail.

Figure 11:
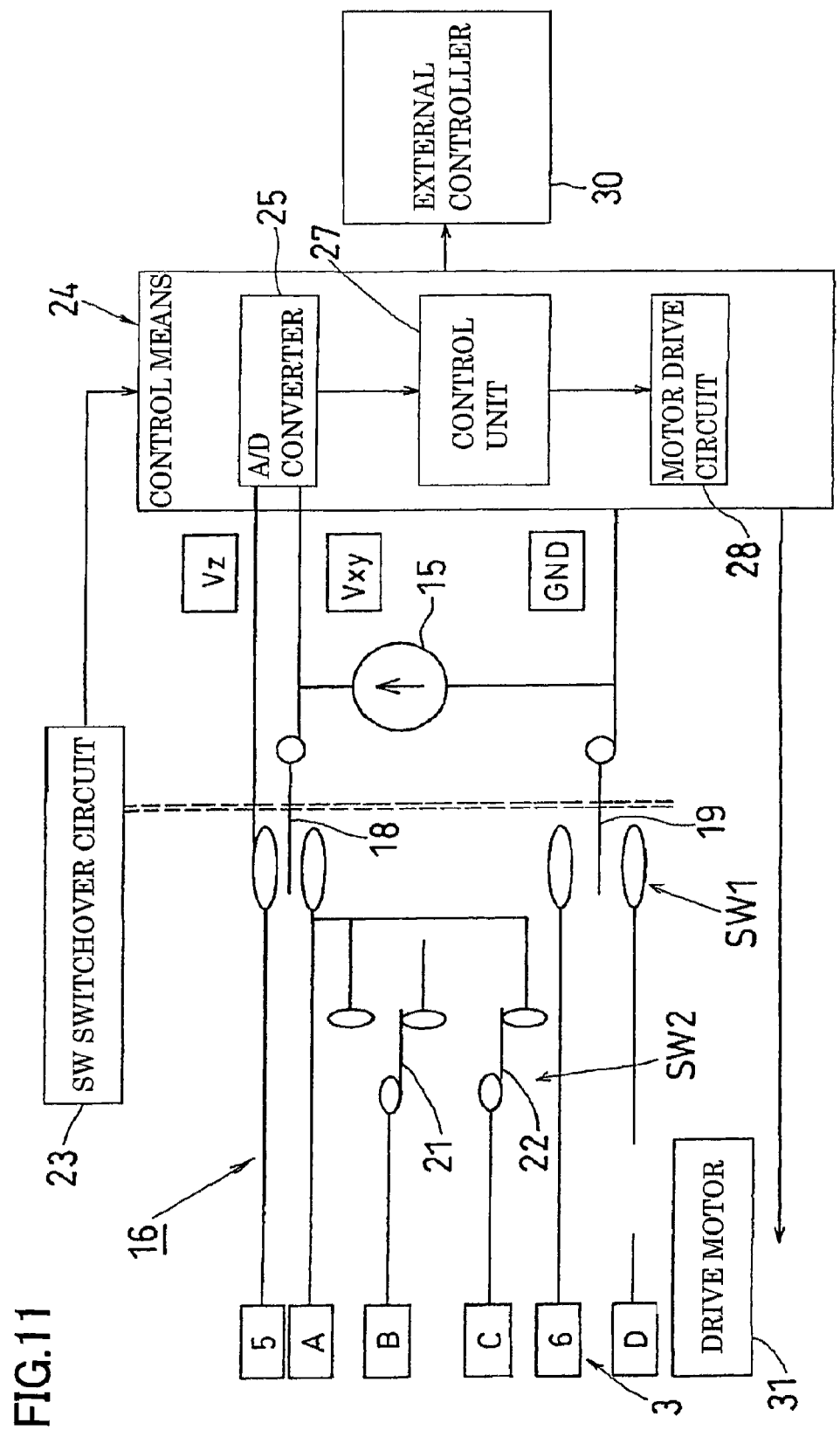
FIG. 11 is a circuit diagram of a tactile sensor application apparatus that shows one embodiment of the present invention.

In FIG. 11, numeral 15 is a constant current power supply, numeral 16 is switch means constructed using an analog multiplexer, equipped with a circuit changing switch SW1 and a circuit changing switch SW2. As also shown in FIGS. 1 and 2, the switch means 16 intervenes between the tactile sensor 3 and control means 24 that will be described later. The circuit changing switch SW1 has a pair of movable contacts 18, 19 that move being interlocked mutually, and is configured to switch over between connecting the constant current power supply 15 to the conductive films 5, 6 side and connecting it to the electrodes A, D side. The circuit changing switch SW2 has a movable contact 21 for connecting the electrode B to the electrode D or the electrode A, and the movable contact 22 for connecting the electrode C to the electrode A or the electrode D, and is configured to switch over between passing a current from the electrodes A, C (the first electrode part 9) to the electrodes B, D (the first electrode part 10) and passing a current from the electrodes A, B (the second electrode parts 11) to the electrodes C, D (the first electrode part 12).

Numeral 23 is a switch switchover circuit, interlocking the circuit changing switches SW1, SW2 to work together so as to perform a switching operation. The numeral 24 is control means that has a control unit 27 including an A/D converter 25, a CPU and memory, and a motor drive circuit 28. Numeral 30 is an external controller made up with a CPU etc. Numeral 31 is a drive motor of the robot 1. As shown in FIG. 1, the drive motor 31 is fixed to a knee part of the leg or an ankle part of the robot 1, being configured to make the lower leg part of the robot 1 swing back and forth or the foot swing back and forth at the ankle part by driving of the drive motor 31. Moreover, as shown in FIG. 2, the drive motor 31 is built in the joint parts of the fingers of the hand, corresponding to each tactile sensor 3 installed onto the fingers of the hand, and makes it possible to move the fingers of the hand at joint parts to grasp and open the hand by driving of the drive motor 31.

In controlling the tactile sensor 3, first, movable contact points 18, 19 of the circuit changing switch SW1 are switched over to the conductive film sides 5, 6 to set so that a current may flow from the constant current power supply 15 to the conductive films 5, 6. Usually, when an object does not contact the tactile sensor 3, since the conductive films 5, 6 are insulated from each other by the spacer etc., in the case where a current is made to flow between the conductive films 5, 6, a maximum voltage Vmax that is set by the constant current power supply 15 occurs between the conductive films 5, 6. Then, by contacting the tactile sensor 3, the conductive films 5, 6 are connected through the pressure sensitive resistance sheet 4, and the voltage Vz occurs between the conductive films 5, 6. From a time when this voltage Vz falls to a predetermined voltage or lower, detection that will be described below will be started.

[Detection of Contact Pressure]

According to an increase of the pressing by a contact to the tactile sensor 3, resistance of the pressure sensitive resistance sheet 4 decreases and the voltage Vz between the conductive films 5, 6 varies. Therefore, in taking out a current from the conductive film 6 after a lapse of a predetermined time from when the voltage Vz became a predetermined voltage Vz0 or lower, a voltage Vz indicating the contact pressure is detected from a difference (combination) between the voltage V5 of the conductive film 5 and a voltage V6 of the conductive film 6, and data converted from it by the A/D converter 25 of the control means 24 is stored in the control unit 27.

[Detection of Contact Coordinates]

Next, movable contacts 18, 19 of the circuit changing switch SW1 are turned to the electrode A, D sides to connect the constant current power supply 15 to the electrode A, D sides. In this occasion, in order that a constant current flows from the constant current power supply 15 to the electrodes A, C (the first electrode part 9) and to the electrodes B, D (the first electrode part 10), in the circuit changing switch SW2, its movable contact 21 is turned to the electrode D side to connect the electrode B and the electrode D and at the same time the movable contact 22 is turned to the electrode A side to connect the electrode A and the electrode C. When making a current flow from the first electrode part 9 and taking the current from the first electrode part 10, a voltage V0x between the first electrode parts 9, 10 that the difference (combination) between the voltage V9 of the first electrode part 9 and the voltage V10 of the first electrode part 10 is inputted into the control means 24 and is converted by the A/D converter 25, and that data is stored in the control unit 27.

At this time, the current flows in the pressure sensitive resistance sheet 4 in the X direction. The voltage Vzx between the conductive film 5 and the electrodes B, D (the first electrode part 10) is detected from a difference (combination) between the voltage V10 of one first electrode part 9 and the voltage V6 of one conductive film 6, and is converted by the A/D converter 25 of the control means 24 similarly. That data is stored in the control unit 27. Since the X coordinate of a contact position indicating the contact position in the X direction is Vzx/V0x, the control unit 27 calculates this to obtain the X coordinate.

Next, when the movable contact 21 of the circuit changing switch SW2 is turned to the electrode A side to connect the electrode A and the electrode B, the movable contact 22 is tuned to the electrode D side to connect the electrode C and the electrode D, and a current is made to flow between the electrodes A, B (the second electrode part 11) and the electrodes C, D (the second electrode part 12); the current flows through the pressure sensitive resistance sheet 4 in the Y direction. Similarly, regarding the Y coordinate of the contact position, when a current is made to flow from the second electrode part 11 and the current is taken in from the second electrode part 12, Vzy/V0y indicating the contact position in the Y direction is calculated by the control unit 27 from a difference (combination) between the voltage V11 of the second electrode part 11 and the voltage V12 of the second electrode part 12 and a difference (combination) between the voltage V11 of the one second electrode part 11 and the voltage V6 of the one conductive film 6, and the data is stored in the memory.

[Detection of Contact Area to Contact Pressure]

A voltage between the electrodes A, C (the first electrode part 9) and the electrodes B, D (the first electrode part 10) is denoted by V0xmax. A voltage V0max between the electrodes A, B (the second electrode 11) and the electrodes C, D (the second electrode 12) was AD converted by the A/D converter 25 of the control means 24 and the data was stored in the control unit 27 in advance. Then, since a contact area to the contact pressure in the X direction and in the Y direction can be expressed by V0max−V0x, V0ymax−V0y, respectively, these pieces of data are calculated by the control unit 27 and the data is stored in the memory.

[The Transfer to External CPU and Motor Control]

Next, the data stored in memory of the control unit 27 is transferred to the external controller 30. At the same time, until there is an instruction of motor driving from the external controller 30, the control unit 27 performs controls of re-detection of the contact pressure of the tactile sensor 3, re-detection of the contact coordinates, and re-detection of the contact length (area) with respect to the contact pressure, and controls driving of respective drive motors 31 so that their variation may become the smallest. Then, when the voltages between the pair of the first electrode parts 9, 10 and between the pair of the second electrode parts 11, 12 becomes more than or equal to predetermined values and a voltage between the one pair of the conductors 5, 6 becomes a predetermined value or more, control of keeping values of the obtained data by the control unit 27 is halted.

According to the embodiment, how much contact pressure is applied at a position of the XY coordinates of the tactile sensor 3 can be detected correctly and quickly. In response to the input information, the drive motors 31 of the fingers of the robot 1 can be made to be operated, and feedback can be done precisely and accurately according to a situation. For example, when human being shakes hands with the robot 1, it becomes possible for the robot 1 to shake hands with a child not strongly but softly. When it is necessary for the robot 1 to declare its intention positively, it shakes hands strongly. It is also possible to convey its intention accurately by controlling even tips of the fingers. In addition to the above, if this is applied to pressure detection of the sole, when a balance is lost at the time of two-foot walking, since variation of the contact pressure of a part of the foot can be detected, it is also possible to employ this for a use for keeping the balance of the robot 1 by minute control.

Figure 12:
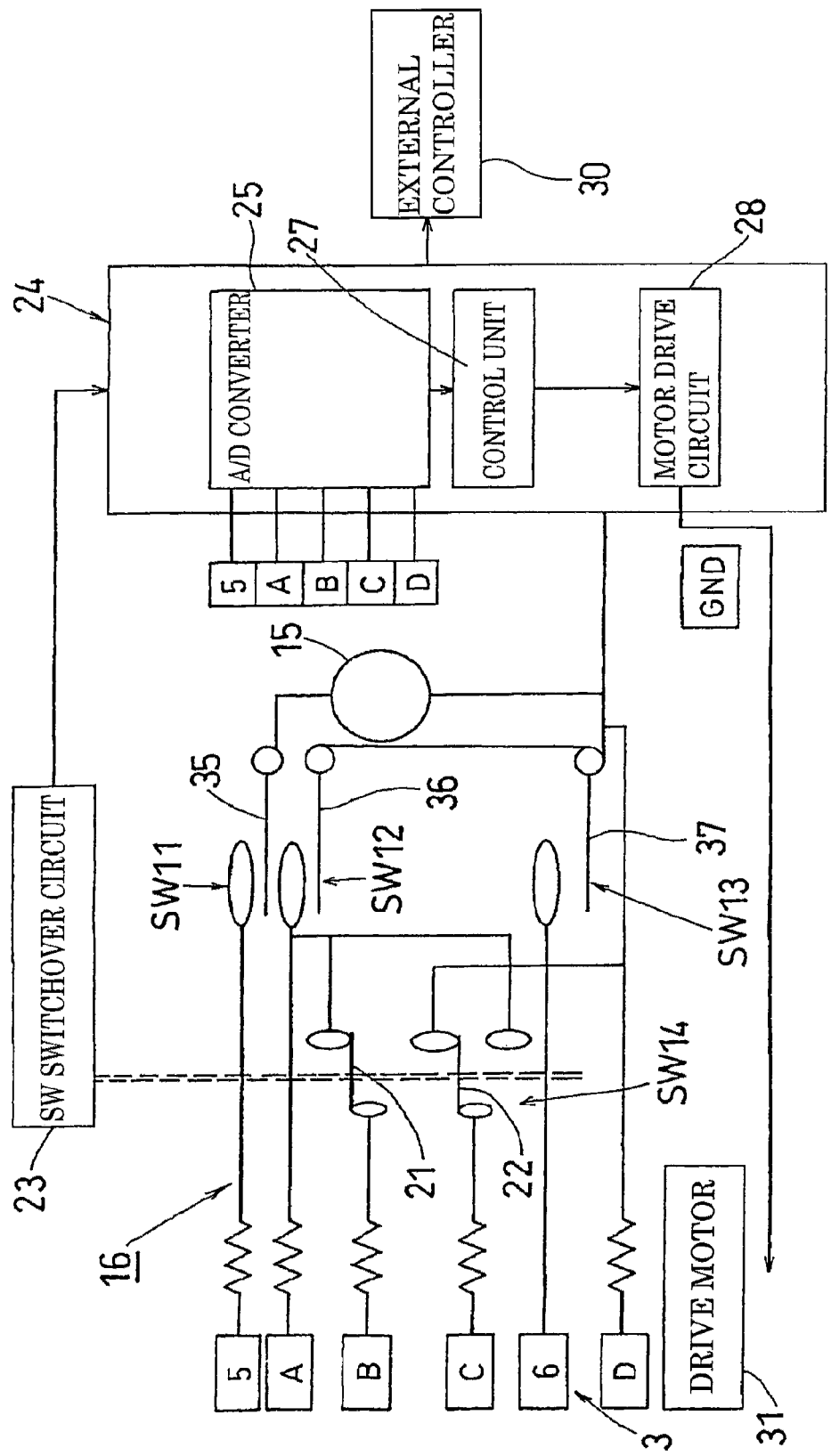
FIG. 12 is a circuit diagram of a tactile sensor application apparatus that shows another embodiment.

FIGS. 12 and 13 show another embodiment, in which instead of the circuit changing switches SW1 and SW2 of the switch means 16 in the above-mentioned embodiment, the switching circuit 16 is provided with a first switch SW11, a second switch SW12, a third switch SW13, and a fourth switch SW14. The first switch SW11 has a movable contact 35, and is so configured that the conductive film 5 may be connected to or disconnected from a high voltage side of the constant voltage power supply 15. The second switch SW12 has a movable contact 36, and is so configured that the first electrode A of the pressure sensitive resistance sheet 4 may be connected to or disconnected from the GND side of the constant voltage power supply 15. The third switch SW13 has a movable contact 37, and is so configured that the conductive film 6 may be connected to or disconnected from the GND side of the constant voltage power supply 15. The fourth switch SW 14 has, like the circuit changing switch SW2, the movable contact 21 that connects the electrode B to either the electrode D or the electrode A, and the movable contact 22 that connects the electrode C to either the connector A or the electrode D, and is configured to switch over between making a current flow from the electrodes A, C (the first electrode part 9) to the electrodes B, D (the first electrode part 10) and making a current flow from the electrodes A, B (the second electrode part 11) to the electrodes C, D (the first electrode part 12). Moreover, the electrodes A, B, C, and D of the conductive films 5, 6 and the pressure sensitive resistance sheet 4 are connected to the A/D converter 25 of the control means 24, and signals (voltages) from the electrode A, B, C and D of the conductive films 5, 6 and the pressure sensitive resistance sheet 4 are configured to be inputted into the A/D converter 25. Other respects in the configuration are the same as the case of the above-mentioned embodiment.

In the case of the present embodiment, the first switch SW11 to the fourth switch SW4 are switched over, as shown in FIG. 13, through the switch switchover circuit 23 by the control unit 27 of the control means 24. That is, FIG. 13 describes an order of switching the first switch SW11 to the fourth switch SW14 in its left end, and the switches are switched in the order of 1, 2, 3, 4, and 5 from a lower row. "1" of a column of the first switch SW11 indicates a state where the conductive film 5 is connected to the high voltage side of the constant voltage power supply 15, and "0" indicates a state where the conductive film 5 is disconnected to the high voltage side of the constant voltage power supply 15. "1" of a column of the second switch SW12 indicates a state where the first electrode A of the pressure sensitive resistance sheet 4 is connected to the GND side of the constant voltage power supply 15, and "0" indicates a state where the first electrode A of the pressure sensitive resistance sheet 4 is disconnected to the GND side of the constant voltage power supply 15. "1" of a column of the third switch SW13 indicates a state where the conductive film 6 is connected to the GND side of the constant voltage power supply 15, and "0" indicates a state where the conductive film 6 is disconnected from the GND side of the constant voltage power supply 15. "1" of a column of the fourth switch SW14 indicates a state where the current is switched from the electrodes A, C (the first electrode part 9) to the electrodes B, D (the first electrode part 10) to make it flow there, and "0" indicates a state where the current is switched from the electrodes A, B (the second electrode part 11) from the electrodes C, D (the first electrode part 12) to make it flow there.

By the control of the control unit 27, the first switch SW11 to the fourth switch SW 14 are switched over through the switch switchover circuit 23. First, the first switch SW11 to the fourth switch SW14 become a state of "1, 1, 1, 1." As in the case of the embodiment, detection of the pressing of the Z coordinate is performed. Next, the first switch SW11 to the fourth switch SW14 are switched over to a state of "1, 1, 0, 1," and the detection of the contact area is performed as in the case of the embodiment. Next, after the first switch SW11 to the fourth switch SW14 were switched over to a state of "1, 0, 0, 1," they are switched over further to a state of "1, 0, 0, 1", where the Y coordinate detection is performed as in the case of the embodiment, and finally, the first switch SW11 to the fourth switch SW14 are switched over to a state of "0, 0, 0, 0", where the X coordinate detection is performed as in the case of the embodiment.

Therefore, also in the case of the present embodiment, as in the case of the above-mentioned embodiment, how much contact pressure is applied at a position of the XY coordinate of the tactile sensor 3 can be detected correctly and quickly. In response to the input information, drive motors 31 of the fingers of the robot 1 are operated and feedback can be performed precisely and accurately according to a situation.

Figure 14:
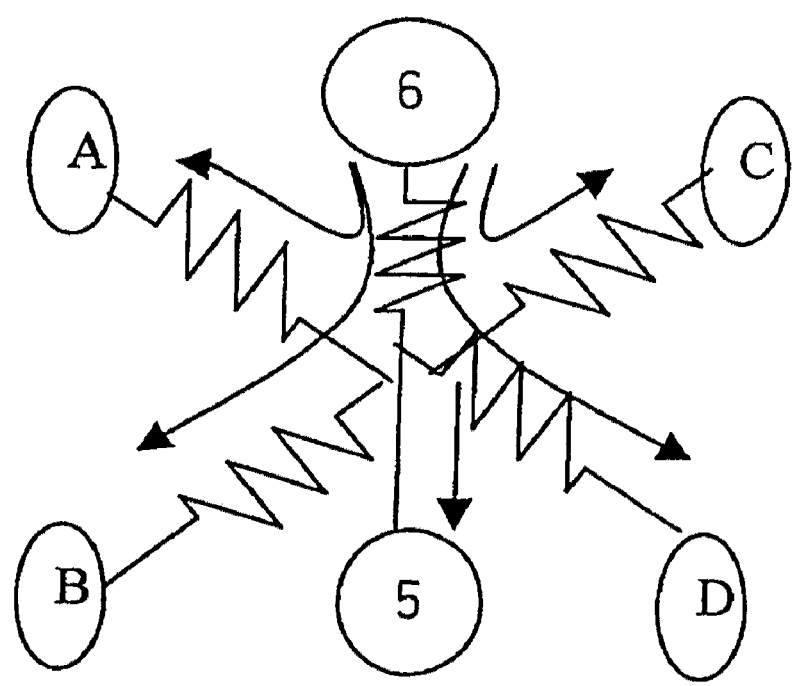
FIG. 14 is an equivalent circuit of a pressure sensitive resistance sheet for showing another method, such as pressure detection.

Note that in the above-mentioned embodiment, a control is switched over between the case where a current is made to flow in the conductive films 5, 6 to perform pressure detection and the case where a current is made to flow in the electrode parts 9, 10, 11, and 12 to obtain the contact coordinates by the switch means 16. However, a method of detecting a pressure and obtaining contact coordinates is not restricted to the case of the embodiment. For example, by connecting the power supply 15 to the conductive film 6, as shown in FIG. 14, making a current flow from the conductive film 6, and taking out the current simultaneously from the electrode parts 9, 10, 11, and 12 of the pressure sensitive resistance sheet 4 and the conductive film 5 at the contact position, the following can be performed. A pressure is detected by the voltage V5 of the conductive film 5 and the voltage V6 of the conductive film 6. A contact position in the X direction is obtained from the voltage V6 of the conductive film 6 and the voltages VA, VC of the electrodes A, C using an expression {(V6−VA)/(V6−VC)}. A contact position in the Y direction is obtained from the voltage V6 of the conductive film 6 and the voltages VB, VD of the electrodes B, D using an expression {(V6−VB)/(V6−VD)}. Therefore, by combining the voltages of the electrode parts 9, 10, 11, and 12 (electrodes A, B, C, and D) and the voltages of the conductive films 5, 6, the pressure detection, the position coordinate detection, and the contact length detection can also be performed without needing switching means.

Moreover, although in the embodiment, the direct-current constant power supply is applied in order to explain the principle plainly, a simple constant current power supply may be realized using a constant voltage power supply and a resistor. Moreover, it is also possible to use an alternating current power supply for a method of reducing noise components by extracting only a signal of a predetermined frequency component.

Incidentally, although in the above-mentioned embodiment, the pressure sensitive resistance sheet 4 is formed in the shape of a rectangle, the shape of the pressure sensitive resistance sheet 4 is not restricted to this and it is also possible to form it in the shape of a disc or in other shapes. Moreover, corresponding to the shape of the pressure sensitive resistance sheet 4, the one pair of conductive films 5, 6 may be formed in the shape of a disc or in other shapes. Moreover, in the case where the first electrode A, the second electrode B, the third electrode C, and the fourth electrode D are provided in four corner parts of the pressure sensitive resistance sheet 4, respectively, and the first electrode part 9, the first electrode part 10, the second electrode part 11, and the second electrode part 12 are constructed with these electrodes A, B, C, and D, the pressure sensitive resistance sheet 4 is not restricted to be in the shape of a rectangle. For example, a roughly square shape with four sides of the pressure sensitive resistance sheet 4 each in a concave bow shape, a roughly square shape with four sides each in a protruded bow shape, and other shapes may be adopted.

Moreover, although the pair of conductive films 5, 6 arranged so as to sandwich the pressure sensitive resistance sheet 4 from the both sides in the thickness direction are used as conductors for passing a current in the resistance in the Z direction provided on the surface of the pressure sensitive resistance sheet 4, instead of this, a pair of conductor for sandwiching the pressure sensitive resistance sheet 4 from the both sides may be constructed with thin copper plates or other things. Moreover, three or more conductors for passing a current through the resistance in the Z direction of the pressure sensitive resistance sheet 4 may be provided on the both sides of the surface in the thickness direction of the pressure sensitive resistance sheet 4.

Moreover, in the above-mentioned embodiment, when a current is made to flow from the conductive film 5 and the current is taken out from the conductive film 6, a contact pressure is obtained from the difference (combination) between the voltage V5 of the conductive film 5 and the voltage V6 of the conductive film 6; when a current is made to flow from the first electrode part 9 and the current is taken out from the first electrode part 10, the contact position in the X direction is obtained from the difference (combination) between the voltage V9 of the first electrode part 9 and the voltage V10 of the first electrode part 10 and the difference (combination) between the voltage V9 of the one first electrode part 9 and the voltage V6 of the one conductive film 6; and when a current is made to flow from the second electrode part 11 and the current is taken out from the second electrode part 12, the contact position in the Y direction is obtained from the difference (combination) between the voltage V11 of the second electrode part 11 and the voltage V12 of the first electrode part 12 and the difference (combination) between the voltage V11 of the one second electrode part 11 and the voltage V6 of the one conductive film 6. However, a method of obtaining the contact pressure, the contact position in the X direction and the contact position in the Y direction is not restricted to this. For example, contrary to the above-mentioned embodiment, when a current is made to flow from the conductive film 6 and the current is taken out from the conductive film 5, naturally, it is all right that the contact pressure is intended to be obtained from the difference (combination) between the voltage V6 of the conductive film 6 and the voltage V5 of the conductive film 5. Moreover, when the current is made to flow from the first electrode part 10 and the current is taken out from the first electrode part 9, naturally, it is all right that the contact position in the X direction is intended to be obtained from the difference (combination) between the voltage V10 of the first electrode part 10 and the voltage V9 of the first electrode part 9 and a difference (combination) between the voltage V10 of the first electrode part 10 and the voltage V5 of the conductive film 5. Moreover, when a current is made to flow from the second electrode part 12 and the current is taken out from the second electrode part 11, naturally it is all right that the contact position in the Y direction is configured to be obtained from a difference (combination) between the voltage V12 of the second electrode part 12 and the voltage V11 of the second electrode part 11 and a difference (combination) between the voltage V12 of the second electrode part 12 and the voltage V5 of the conductive film 5. Moreover, although in a case of the embodiment of FIG. 14, by making a current flow from the conductive film 6 and taking out the current simultaneously from the electrode parts 9,10,11 and 12 of the pressure sensitive resistance sheet 4 and the conductive film 5 of the contact position, it is configured that the pressure is detected and the contact coordinate position is obtained, instead of this, it may be adopted that by making a current flow from the conductive film 5 and taking out the current simultaneously from the electrode parts 9,10, 11 and 12 of the pressure sensitive resistance sheet 4 and the conductive film 6, the pressure is detected and the contact coordinate position is obtained. Furthermore, since both the contact position in the X direction and the contact position in the Y direction are not necessarily required to be detected, and it is enough for either one of the contact positions to be detected, after all, the method of obtaining the contact pressure and the contact position is such that, when a current is made to flow from any one of the electrode parts 9,10,11 and 12 and the conductors 5, 6 and the current is taken out from the remaining electrode parts 9, 10, 11 and 12 and the conductors 5,6, the contact pressure and at least one contact position of the contact position in the X direction and the contact position in the Y direction are obtained from a combination of the voltages V9, V10, V11, and V12 of the at least one pair of the electrode parts 9, 10, 11 and 12 and the voltages V5, V6 of the at lest one pair of the conductors 5, 6.

Moreover, in the above-mentioned embodiment, although the contact pressure detection for obtaining the contact pressure is performed, the contact position detection for obtaining the contact position in the X direction is performed, the contact position detection for obtaining the contact position in the Y direction is performed, the contact length (area) detection for obtaining the contact length in the X direction is performed, and the contact length (area) detection for obtaining the contact length in the Y direction is performed; it is not necessary to perform all the detection of these five kinds. As necessary, one or a plurality of detection can be omitted. For example, it is all right that two of the contact pressure detection for obtaining the contact pressure and the contact position detection for obtaining the contact position in the X direction are performed. It is all right that two of the contact pressure detection for obtaining the contact pressure and the contact position detection for obtaining the contact position in the Y direction are performed. It is all right that two of the contact pressure detection for obtaining the contact pressure and the contact length (area) detection for obtaining the contact length in the X direction are performed. It is all right that two of the contact pressure detection for obtaining the contact pressure and the contact length (area) detection for obtaining the contact length in the Y direction are performed. It is all right that two of the contact position detection for obtaining the contact position in the X direction and the contact length (area) detection for obtaining the contact length in the X direction are performed. It is all right that two of the contact position detection for obtaining the contact position in the X direction and the contact length (area) detection for obtaining the contact length in the Y direction are performed. It is all right that two of the contact position detection for obtaining the contact position in the Y direction and the contact length (area) detection for obtaining the contact length in the X direction, or two of the contact position detection for obtaining the contact position in the Y direction and the contact length (area) detection for obtaining the contact length in the Y direction are performed.

Moreover, in the above-mentioned embodiment, the first electrode A, the second electrode B, the third electrode C, and the fourth electrode D are provided in four corner parts of the pressure sensitive resistance sheet 4, respectively, and with these electrodes A, B, C, and D, the one pair of the first electrode parts 9, 10 for passing a current through the pressure sensitive resistance sheet 4 in the X direction and the one pair of the second electrode parts 11, 12 for passing a current through the pressure sensitive resistance sheet 4 in the Y direction are constructed. However, the one pair of the first electrode parts 9, 10 for passing a current through the pressure sensitive resistance sheet 4 in the X direction and the one pair of the second electrode parts 11, 12 for passing a current through the pressure sensitive resistance sheet 4 in the Y direction are not restricted to have such a construction. For example, it is also possible to construct the pair of the first electrode parts 9, 10 or the pair of the second electrode parts 11, 12 with one or three dot electrodes or more, respectively. Moreover, in the above-mentioned embodiment, although a construction of the first electrode parts 9, 10 and the second electrode parts 11, 12 is set to be the same as the five line type control method that is used in conventional touch panel detection methods, seven line type and eight line type control method more than five line type can be adopted with a modified electrode structure.

Moreover, although in the tactile sensor application apparatus shown in FIG. 11 or FIG. 12 in the above-mentioned embodiment, in order to simplify the explanation, the motor drive circuit 28 of the robot 1 is configured to be driven and controlled based on a detection output of one tactile sensor 3 among a plurality of tactile sensors 3 installed in the robot (controlled apparatus) 1, instead of this, it may be adopted to drive or control one or the plurality of motor drive circuits 28 etc. of the robot 1 based on detection outputs of the plurality of the tactile sensors 3, and thereby control the robot 1 based on the detection output that is combined outputs of the plurality of tactile sensors 3. Moreover, conversely, it may be adopted further to install only one tactile sensor 3 in the robot (controlled apparatus) 1 and drive/control the motor drive circuit 28 of the robot 1 based on a detection output of this one tactile sensor 3.

Moreover, although in the above-mentioned embodiment, the robot 1 is driven/controlled as a tactile sensor application apparatus that uses a tactile sensor 3, the tactile sensor application apparatus using the tactile sensor 3 is not restricted to driving/controlling of the robot 1. For example, it may be all right that a chair for care, a bed for care, air bag equipment, or the like is used being controlled as a controlled apparatus, and they are controlled based on the detection output of the tactile sensor 3.

INDUSTRIAL APPLICABILITY

The present invention can be used as an apparatus for the robotic tactile sensor and an apparatus for controlling a chair, or a bed by detecting a pressure applied on it.

The invention claimed is:

1. A tactile sensor, comprising:
   a pressure sensitive sheet having a length in an x direction, a width in a y direction and a thickness in a z direction, the pressure sensitive sheet providing an electrical resistance;
   at least one pair of electrode parts on a peripheral part of the pressure sensitive sheet for passing a current through the pressure sensitive sheet in at least one of the x direction and y direction; and
   a pair of electrically conductive sheets provided on opposite surfaces in the thickness direction of the pressure sensitive sheet for passing a current between the pair of electrically conductive sheets through the pressure sensitive sheet only in the z direction, the electrically conductive sheets being on opposite sides of the pressure sensitive sheet;
   wherein the pair of electrically conductive sheets are coextensive with the pressure sensitive sheet, wherein surfaces of the pair of electrically conductive sheets facing the pressure sensitive sheet have electrical conductivity, and
   wherein the pressure sensitive sheet is sandwiched from both sides in the thickness direction by the pair of electrically conductive sheets for passing the current through the pair of electrically conductive sheets only in the z direction when any part inside the peripheral part of the pressure sensitive sheet is pressed.

2. The tactile sensor of claim 1, wherein the pair of electrically conductive sheets are insulated from one another in the absence of pressure and electrically connected through the pressure sensitive sheet when pressure is applied to the pressure sensitive sheet.

3. The tactile sensor of claim 1, wherein the at least one pair of electrode parts comprises electrodes in the pressure sensitive sheet.

4. The tactile sensor of claim 1, wherein the at least one pair of electrode parts are opposite each other in the x direction on the peripheral part of the pressure sensitive sheet for passing a current in the x direction, a first electrode part of the pair of electrode parts providing a plurality of electrodes apart from each other in the y direction, a second electrode part of the pair of electrode parts providing a plurality of electrodes apart from each other in the y direction.

5. The tactile sensor of claim 1, wherein the at least one pair of electrode parts are opposite each other in the y direction on the peripheral part of the pressure sensitive sheet for passing a current in the y direction, a first electrode part of the pair of electrode parts providing a plurality of electrodes apart from each other in the x direction, a second electrode part of the pair of electrode parts providing a plurality of electrodes apart from each other in the x direction.

\* \* \* \* \*